US006792793B2

(12) United States Patent
Mendoza

(10) Patent No.: US 6,792,793 B2
(45) Date of Patent: Sep. 21, 2004

(54) BREATH MEASUREMENT INSTRUMENT AND BREATH ALCOHOL INTERLOCK DEVICE INCORPORATING SAME

(75) Inventor: Joaquin L. Mendoza, San Jose, CA (US)

(73) Assignee: Ignition Lock International, Apple Valley, CA (US)

( * ) Notice: Subject to any disclaimer, the term of this patent is extended or adjusted under 35 U.S.C. 154(b) by 59 days.

(21) Appl. No.: 10/108,906

(22) Filed: Mar. 28, 2002

(65) Prior Publication Data

US 2003/0183437 A1 Oct. 2, 2003

(51) Int. Cl.[7] .......................... G01N 1/22; G01N 31/00; G01N 33/497; B60K 28/06; A61B 5/097
(52) U.S. Cl. .......................... 73/23.3; 422/84; 436/132; 436/900; 600/532; 600/543; 180/272; 340/576
(58) Field of Search .......................... 73/23.3; 180/272; 340/576; 422/84; 436/132, 900; 600/529, 532, 538, 543

(56) References Cited

U.S. PATENT DOCUMENTS

| 3,780,311 | A | * | 12/1973 | Brown .......................... 307/10.6 |
| 3,823,382 | A | | 7/1974 | Gaddy |
| 3,824,537 | A | | 7/1974 | Albertson |
| 3,824,538 | A | | 7/1974 | Slemp |
| 3,831,707 | A | | 8/1974 | Takeuchi .......................... 307/10.1 |
| 4,039,852 | A | | 8/1977 | Miyamoto et al. |
| 4,104,688 | A | | 8/1978 | Pecsi |
| 4,533,016 | A | | 8/1985 | Betton |
| 4,592,443 | A | | 6/1986 | Simon .......................... 180/272 |
| 4,607,719 | A | | 8/1986 | Rugis et al. .......................... 180/272 |
| 4,611,290 | A | | 9/1986 | Henningsen et al. |
| 4,613,845 | A | | 9/1986 | Du Bois |
| 4,689,603 | A | | 8/1987 | Conigliaro et al. |
| 4,697,666 | A | * | 10/1987 | Collier et al. .......................... 180/272 |
| 4,809,810 | A | | 3/1989 | Elfman et al. .......................... 180/272 |
| 4,926,164 | A | | 5/1990 | Porter et al. .......................... 340/576 |
| 4,996,161 | A | | 2/1991 | Conners et al. |
| 5,020,628 | A | | 6/1991 | Bigliardi et al. .......................... 180/272 |
| 5,426,415 | A | | 6/1995 | Prachar et al. .......................... 340/576 |
| 5,531,225 | A | | 7/1996 | Nawata et al. |
| 5,563,576 | A | | 10/1996 | Drori et al. |
| 5,929,319 | A | | 7/1999 | King et al. .......................... 73/23.3 |
| 6,026,674 | A | | 2/2000 | Gammenthaler .......................... 73/19.01 |

* cited by examiner

Primary Examiner—Daniel S. Larkin
(74) Attorney, Agent, or Firm—Denton L. Anderson; Sheldon & Mak

(57) ABSTRACT

A breath measurement instrument using a combination of breath pressure, temperature, and humidity measurements to determine whether or not breath samples are human and properly delivered. Valid samples require maintenance of a threshold dynamic pressure of a sample being introduced for a predetermined time, a valid temperature of the sample and a valid humidity of the sample, wherein the range of valid sample temperatures is adjusted according to a measured sample humidity. Also disclosed is a breath alcohol instrument having an alcohol-specific fuel cell and a fuel cell circuit for generating a breath alcohol signal. Further disclosed is an interlock system for inhibiting operation of machinery such as a vehicle, and a method for screening breath samples and determining an alcohol content thereof.

26 Claims, 6 Drawing Sheets

BREATH MEASUREMENT INSTRUMENT AND BREATH ALCOHOL INTERLOCK DEVICE INCORPORATING SAME

BACKGROUND

The present invention relates to breathalyzers, and breath alcohol interlock devices for preventing operation of vehicles and other machines by intoxicated persons.

In the 19th century, law enforcement officials dealt with the problem of alcohol abusers by imprisoning them until they were sober. In the 20th century, the advent of high-speed transportation and complex machinery gave high priority to alcohol testing and screening. Automobiles traveling at ninety feet per second on the freeway are unforgiving of drivers with alcohol impairment. The same is true for a 300-passenger aircraft guided by an alcohol-impaired pilot attempting to land under minimum-visibility conditions. There is very little margin for error. People who operate complex equipment with their judgment impaired by alcohol may not only be a danger to themselves, but impact the safety of others.

Until recently, the main application of alcohol testing was to traffic law enforcement. The intent was to identify people suspected of driving under the influence of alcohol and remove them from the road. After arrest, law enforcement officers gave the subject a chemical test to determine his blood alcohol level. Subjects were either released or incarcerated and prosecuted, depending on what alcohol levels were illegal as dictated by state law. Until the mid-1940's, the primary means of measuring blood alcohol levels involved either blood or urine sample testing, both of which were time-consuming and expensive procedures. In the late 1940's, alcohol breath testing replaced blood and urine sample testing as a means of screening subjects and producing evidentiary results for prosecution.

In the 1980's, railroad, nuclear, Department of Defense, and maritime employees came under Federally-mandated testing requirements. In each case, new laws followed a major, alcohol-related disaster. In 1991, the United States Congress passed the Omnibus Transportation Employee Testing Act. This legislation mandated alcohol testing for transportation personnel involved in safety-sensitive jobs. This mandate included airline pilots and cabin attendants, truck drivers, railroad crews, and gas pipeline workers. The US Department of Transportation further defined unacceptable maximum alcohol levels.

Since the mid-1980s, infrared (IR) technology has been the primary means of breath alcohol testing in the United States. Current technology uses infrared measurement systems that are made more specific for alcohol by using several optical filters. Breath alcohol levels are measured this way by passing a narrow band of IR light, selected for its absorption by alcohol, through one side of a breath sample chamber and detecting emergent light on the other side. The alcohol concentration is then determined by using the well-known Lambert-Beers law, which defines the relationship between concentration and IR absorption. This IR technology has the advantage of making real-time measurements; however, it is particularly difficult and expensive to achieve specificity and accuracy at low breath alcohol concentration levels. Also, the IR detector output is nonlinear with respect to alcohol concentration and must be corrected by measurement circuits. A more favored technology uses electrochemical cells, also known as fuel cells.

The fuel cell effect was discovered in the early 1800's when a British scientist immersed two platinum electrodes in sulfuric acid electrolyte and supplied hydrogen at one electrode and oxygen at the other. The resulting reaction created a current flow between the electrodes. There was no practical application of fuel cells at that time because of high cost and technological problems. In the 1960s, researchers at the University of Vienna demonstrated a fuel cell that was specific for alcohol. This evolved into the present-day cell used in all fuel cell-based breath alcohol measurement instruments. In its simplest form, the alcohol fuel cell consists of a porous, chemically inert layer coated on both sides with finely divided platinum (called platinum black). The porous layer is impregnated with an acidic electrolyte solution, and platinum wire electrical connections are attached to the platinum black surfaces, and this assembly is mounted in a plastic case having a gas inlet that allows a breath sample to be introduced as shown in FIG. 1.

The exact chemistry of the reaction that takes place in an alcohol fuel cell is open to some conjecture. Researchers assume that the reaction converts alcohol to acetic acid. In the process, this conversion produces two free electrons per molecule of alcohol. This reaction takes place on the upper surface of the fuel cell. H+ ions are freed in the process, and migrate to the lower surface of the cell, where they combine with atmospheric oxygen to form water, consuming one electron per H+ ion in the process. Thus, the upper surface has an excess of electrons, and the lower surface has a corresponding deficiency of electrons. When the two surfaces are connected electrically, a current flows through this external circuit to neutralize the charge. This current is a direct indication of the amount of alcohol consumed by the fuel cell. With appropriate signal processing, breath alcohol concentrations directly can be displayed. Commercial fuel cell instruments, introduced in the mid-1970s and initially suitable for non-evidential alcohol breath testing, were improved sufficiently by 1980 to be certified for evidential use by the US Department of Transportation, and by a number of state agencies and foreign governments. The fuel cell has established a reputation for specificity and linearity of response over the complete range of alcohol concentration expected in the breath. This range is from 5 to 900 ppm or its equivalent in other units of measurement.

When a precise volume of breath sample is quickly introduced into a fuel cell, the output current from the cell rises from zero to a peak, and then ultimately decays back to zero. The rate at which this happens is highly dependent on the loading across the sensor terminals. FIG. 2 illustrates this effect, for loadings of 100 and 300 ohms, and for a shorted condition (0 ohms). Traditional fuel cell measurement instruments of the prior art have load resistors of several hundred to one thousand ohms, and the height of the voltage peak across the resistor is used as the measure of alcohol content of the sample. Although this technique produces good linearity, significant time elapses before an acceptable measurement can be obtained, and the measurement cycles are objectionably long because complete conversion of alcohol to electric current must occur prior to a new cycle, the current being limited by the load resistance of the measurement circuit.

More recent instruments have utilized lower load resistance to shorten the time to reach the peak output and speed up the recovery time, and they integrate the output signal to obtain enhanced accuracy. However, the number of positive samples analyzed in rapid succession with these prior art instruments still had to be strictly limited. Successive readings might be in error as peak fuel cell output decreased because of the time required for the cell to complete the alcohol conversion reaction. This could conceivably give readings beyond the acceptable limits for evidential measurement. In a typical unit, ten successive measurements of 0.100 gm/dl gas at three minutes between readings might result in the tenth reading being 0.095 or 0.094. Accordingly, these instruments have unfortunately been limited to no more than five positive tests per hour for maintenance of evidential accuracy. Consequently, only one subject could be tested per hour with evidential accuracy in those jurisdictions requiring two tests per subject, and a third test if the first two differed by more than a given amount, and an additional a test reading on a standard to verify calibration of the instrument. In addition, once the fuel cell output of these instruments decreases due to repeated testing, an extended period of time (up to sixteen to twenty-four hours) is required before there is full recovery to the initial output.

Another problem with operating the fuel cell in the conventional mode with a load resistor is that although the output is very linear up to alcohol levels of about 0.150 gm/dl, the readings are increasingly low at higher levels. Thus the cell reads 2–3% low at 0.200 gm/dl, and 5–6% low at 0.300 gm/dl. This was of very little practical significance where legal maximum blood alcohol levels were fixed at 0.100 or 0.080, but it was a subject of criticism.

In early 1986, in a further investigation of fuel cell output measurement, based on a supposition that the entire signal from the fuel cell, rather than just the peak value, might be useful. The integrated output might contain enough information so that when the signal was analyzed properly, the effects of memory and high alcohol level nonlinearity might be minimized. Table 1 shows the results of a study made early in 1994. The investigators used a compressed gas standard with 0.100 ethanol concentration. The investigators made tests three minutes apart, at an ambient temperature of 23° C. While the peak value varies by 13%, the calibrated fuel cell output integral remains constant.

TABLE 1

Normalized Peak Value vs. Calibrated Integral

| Peak Value | Integral |
|---|---|
| 0.100 | 0.1009 |
| 0.0971 | 0.1008 |
| 0.0950 | 0.1006 |
| 0.0934 | 0.1004 |
| 0.0921 | 0.1010 |
| 0.0909 | 0.1009 |
| 0.0899 | 0.1008 |
| 0.0889 | 0.1006 |
| 0.0881 | 0.1004 |
| 0.0873 | 1.0004 |

It is also known to operate the fuel cell with the output essentially short-circuited, which gives the fastest response as shown in FIG. 2. With this configuration, cell output peaks in two to five seconds and typically returns to zero by the time that a cell with a 300-ohm load is reaching its peak value. In this mode, the fall-off in peak values from test to test is much worse than in the mode with a resistor; however, by integrating the entire area under the curve, the slump in reading from test to test is virtually eliminated. Because the cell has already returned to zero output, it is ready for another test without an additional waiting for a cleanup period to complete the reaction. The readings also recover much more quickly after a series of tests. For practical purposes, the number of tests per hour is limited by the recycling time of the test instrument and test protocols rather than the performance of the fuel cell. Research also established that a cell used in this mode is capable of linear response out to 0.400 gm/dl with an error no greater than 2%. For example, the linearity of a cell that was linear up to 0.150 gm/dl in a conventional voltage mode is preserved out to 0.400 gm/dl or more. A prior art circuit that provides an analog output in response to a fuel cell being loaded selectively with 330 ohms of resistance or essentially a short circuit is shown in FIG. 3, the short circuit being applied in response to an external signal.

Studies made by the Transportation Research Board concluded that blood alcohol concentrations (BAC) below 0.050% may impair driving-related skills. Further testing has shown that instruments using fuel cells showed greater accuracy at low BACs than the instruments using infrared techniques. In yet additional tests, investigators at the University of Tennessee at Memphis measured the response of fuel cell-based alcohol breath testing instruments to various substances including many that might be expected to be present in the breath of individuals being tested. In addition to separate responses to various non-alcoholic substances, ethanol, methanol, and isopropanol were separately introduced at alcohol concentrations of 0.1 gm/dl. The results indicate generally that the sensitivity to the non-alcoholic substances was from zero to about 2%; for ethanol the response was 100%; and for methanol and isoproponal the response was about 45%.

Notwithstanding the above developments, the breath alcohol instruments and interlock devices of the prior art are not entirely satisfactory, typically exhibiting one or more of the following disadvantages:

1. They are ineffective in distinguishing human breath samples, properly delivered, from non-human and/or improperly delivered samples; and 2. They are unreliable in that they are adversely affected by variations in ambient pressure (altitude) and temperature, as well as by the temperature and/or humidity of breath samples.

Although it is known to require a threshold dynamic pressure of the sample as well as to require a valid range of temperature and humidity of the sample, calibration of the instruments of the prior art to reject all non-human samples often results in unwanted rejection of proper human samples, and vice-versa. Also, even with breath samples properly accepted as human, there is still a likelihood of significant error in measured breath alcohol levels due variations in ambient conditions as well as the temperature and humidity of breath samples, even when the temperature and humidity are within prescribed limits and dynamic pressure maintained over a full required duration of time.

Thus there is a need for a breath alcohol interlock device that avoids the disadvantages of the prior art.

SUMMARY

The present invention meets this need by providing a breath alcohol interlock device that is particularly effective in distinguishing permitted from disallowed alcohol levels, having quick response characteristics, and is both easy to operate and inexpensive to provide. In one aspect of the invention, a breath measurement instrument includes means for receiving a breath sample; and means for validating the sample, including means for determining a sample temperature of the sample, means for determining a moisture content of the sample, and means for comparing the determined sample temperature and moisture content with a predetermined profile of valid temperatures and moisture contents, validation being blocked unless the determined temperature and moisture content is within the predetermined profile, wherein the predetermined profile includes a valid range of the determined sample temperature that is dependent on the determined sample moisture content. The means for receiving the breath sample can include a tubular conduit having a mouthpiece extremity, the conduit defining a sample passage. The means for determining the sample temperature can include a temperature sensor supported relative to the tubular conduit and projecting into the sample passage, a sample temperature circuit having a sample temperature output, and means for signifying at least an out-of-limit temperature, and an in-limit temperature of the breath sample. The means for determining humidity can include a humidity sensor supported relative to the tubular conduit and projecting into the sample passage, a humidity circuit having a sample humidity output, and means for signifying at least an out-of-limit humidity and an in-limit humidity, the validation being blocked unless the temperature and humidity outputs are both in-limit. The in-limit humidity can be a first in-limit humidity, the humidity output also being capable of signifying a second in-limit humidity, the in-limit temperature also being a first in-limit temperature, the temperature output also being capable of signifying a second in-limit temperature, at least one combination of in-limit temperature and in-limit humidity being outside of the predetermined profile, that combination blocking the validation. In this way the range of acceptable sample temperatures is advantageously adjusted according the moisture content of the sample for facilitating effective distinguishing of non-human and/or improperly delivered breath samples from valid ones.

The invention also provides a breath alcohol instrument including the breath measurement instrument in combination with means for determining an alcohol content of the sample. The means for determining the alcohol content can include an alcohol-specific fuel cell, and further, a fuel cell circuit for producing a breath alcohol signal, and means for compensating the breath alcohol signal in response to variations in one or more variables of the set consisting of ambient temperature, ambient pressure, sample temperature, and sample humidity.

The invention further provides a breath alcohol interlock device for preventing use of a machine by an intoxicated operator, the device including the breath alcohol instrument in combination with an interlock circuit for disabling the machine except upon validation of a breath sample having an alcohol content below a predetermined amount.

In another aspect of the invention, a method for screening breath samples and determining an alcohol content thereof includes receiving a breath sample; validating the sample by determining a sample temperature of the sample, determining a moisture content of the sample, comparing the determined sample temperature and moisture content with a predetermined profile of valid temperatures and moisture contents, and blocking the validation unless the determined temperature and moisture content is within the predetermined profile, wherein the predetermined profile includes a valid range of the determined sample temperature that is dependent on the determined sample moisture content; determining an alcohol content of the sample by producing a breath alcohol signal responsive to the alcohol content of the sample; and compensating the breath alcohol signal in response to variations in one or more variables of the set consisting of ambient temperature, ambient pressure, sample temperature, and sample humidity.

DRAWINGS

These and other features, aspects, and advantages of the present invention will become better understood with reference to the following description, appended claims, and accompanying drawings, where:

DESCRIPTION

Figure 1:
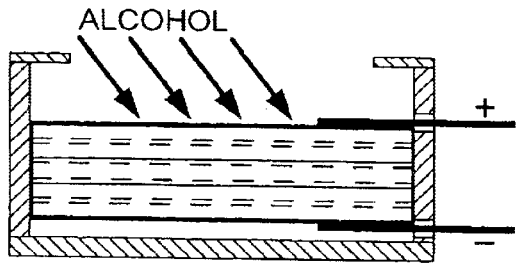
FIG. 1 is a sectional diagram view of a prior art alcohol-specific fuel cell sensor.
Figure 2:
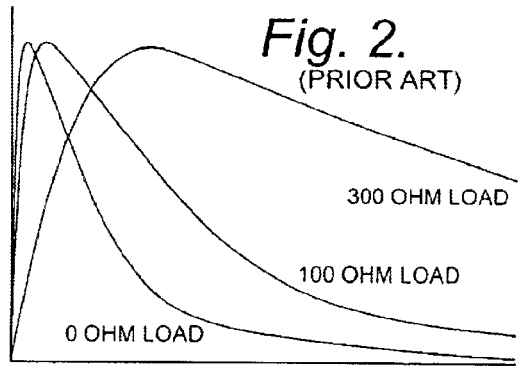
FIG. 2 is a dynamic electrical response profile of the fuel cell sensor of FIG. 1 for various loadings thereof.
Figure 3:
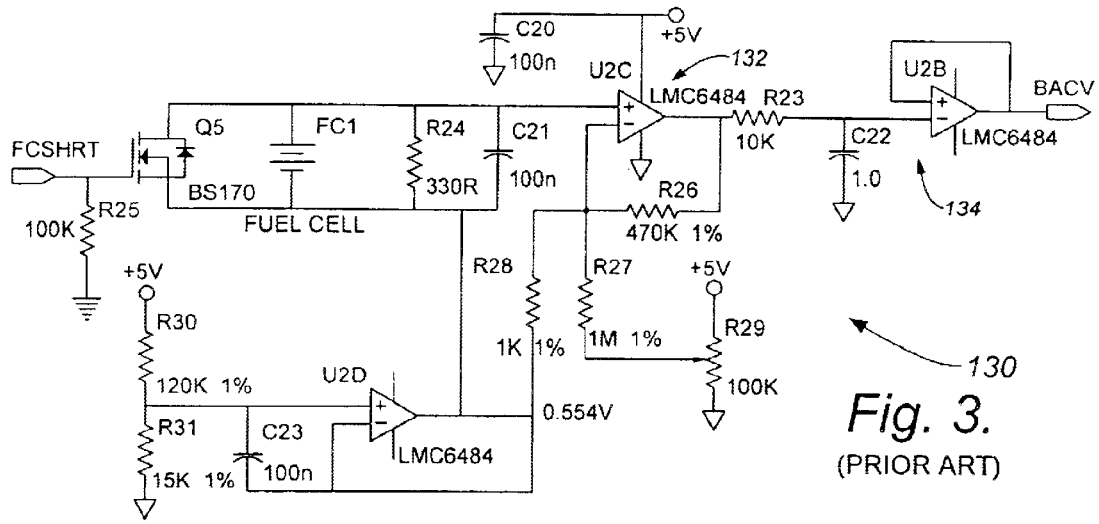
FIG. 3 is a schematic diagram of a prior art circuit for interfacing the fuel cell sensor of FIG. 1.
Figure 4:
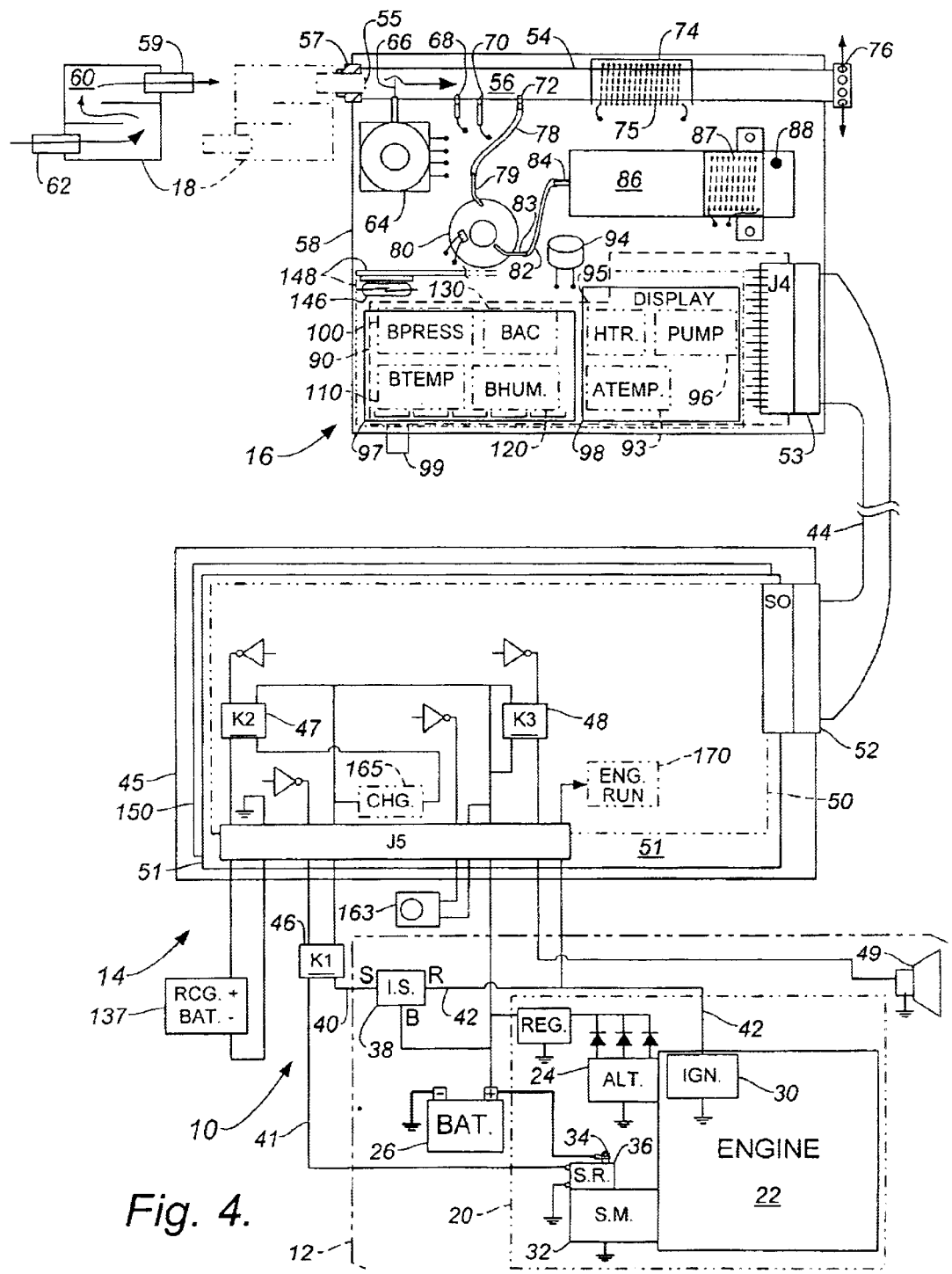
FIG. 4 is a partly pictorial, partly schematic overall system block diagram of a breath alcohol interlock system according to the present invention, the system being installed in equipment having a power plant (such as a vehicle) being protected thereby.

The present invention is directed to a breath alcohol interlock system that is particularly effective in protecting machinery such as vehicles from unauthorized operation by persons having excessively high alcohol intake. With reference to FIGS. 3–12 of the drawings, an interlock system 10 for a vehicle 12 includes a base unit 14 that is connected for conditionally inhibiting operation of the vehicle, and a sample unit 16 that is connected to the base unit and being adapted for receiving through a mouthpiece 18 breath samples from a person intending to drive and/or actually driving the vehicle, as shown in FIG. 4.

The vehicle 12 is shown as having an exemplary power plant 20 including an engine 22 that drives an alternator 24 for charging a vehicle battery 26 through a regulator 28. The engine 22 also has an ignition 30, and a starter motor 32 having a main terminal 34 and an associated starter relay 36. Conventionally, an ignition switch 38 which is powered by the battery 26 has a momentary start terminal 40 for activating the starter relay 36 via a start circuit 41, and a run terminal 42 for powering the ignition 30 through a run circuit 42. Installation of the interlock system 10 typically (but not necessarily) involves breaking the start and circuit 41 to prevent operation of the starter motor 32. It will be understood that other means for preventing (or restricting) operation of the engine 22 are contemplated, such as by breaking the run circuit 42, inhibiting operation of a fuel system (not shown) of the vehicle 12, or any suitable means by which other equipment to be protected by the present invention may be inhibited. Normally, however, preventing continued operation of the engine 22 is sometimes to be avoided, such as when forced termination of such operation has hazard potential. In such situations it is contemplated that the engine 22 (or other motive means) would be disabled only after it was first parked or otherwise stopped subsequent to a failed breath alcohol test.

The base unit 14, which is connected to the sample unit 16 by a signal cable 44, has a housing 43 and circuit interrupting elements therein in the form of first second, and third relays 46, 47, and 48, the first relay 46 (which itself may be located external to the base unit 12 as shown in FIG. 4) being interposed in the start circuit 41 for selectively disabling the starter motor 32 and its starter relay 36 as further described below. The second relay 47 controls connection of a battery charging circuit to a rechargeable battery as described below. The third relay 48 is optional, being connected for activating a horn 49 of the vehicle 12 under certain conditions (without preventing other and conventional activations of the horn), also as further described below. In the exemplary configuration of the system 10 shown in the drawings, the relays 46, 47, and 48 are connected in a power circuit 50 of a power module 51, the electrical connections between the interlock system 10 and the vehicle 12 being through an interface connector J5. The signal cable 44 has a cable plug 52 being connected to a socket SO of the base unit 14, and a cable socket 53 being connected to a plug J4 of the sample unit 16, the power circuit 50 being further described below in connection with FIG. 11.

The sample unit 16 has a sample tube 54 forming an inlet 55 of a sample chamber 56, the inlet 55 being in the form of a resilient grommet 57 that is adapted for sealingly extending the inlet through one wall of a case 58 of the sample unit 16, receiving a projecting outlet 59 of the mouthpiece 18. According to the present invention, the mouthpiece 18 also has a labyrinth chamber 60 for trapping entrained moisture of a breath sample that is introduced through a projecting inlet 62 of the mouthpiece 18. A breath pressure transducer 64 is supported in the case 58 and having a small strain-gage actuator 66 projecting into the chamber 56 a short distance from the inlet 55. A breath temperature sensor 68 also projects into the chamber 56 a short distance from the inlet 55, preferably down stream of the breath actuator 66. Further, a humidity sensor 70 also projects through the sample tube 54 and into the sample chamber 56, the sample tube also having a sample port 72 forming a side exit from the chamber 56 down stream of each of the above-described sensing elements. Downstream of the sample port 72, the sample tube 54 projects through a heat shroud 74 having a tubular heating coil 75, and through an opposite wall of the case 58 to a chamber exhaust outlet 76. The sample tube 54 can be formed by modifying a commercial breath sample tube that is available as Part No. 95-00130, from Alcohol Countermeasure Systems Corp., of Ontario, Canada. The modifications to the sample tube 54 consist of forming openings for the humidity sensor 70, and for any of the breath actuator 66, the breath temperature sensor 68, the humidity sensor 70, and the sample port 72, and installing the heat shroud 74 and its associated heating coil 75.

The sample port 72 is fluid-connected through a flexible inlet conduit 78 to the inlet 79 of an alcohol-specific fuel cell alcohol sensor 80, another flexible outlet conduit 82 being fluid-connected from an outlet 83 of the alcohol sensor to the inlet 84 of a piston pump 86 having a solenoid coil 87. Activation of the solenoid coil 87 moves an internal piston (not shown) of the pump 86 away from the pump inlet 84 so as to draw a gas sample from the sample chamber 56, through the inlet conduit 78 and into the alcohol sensor 80, a portion of the gas being drawn into the pump 86. The piston is biased toward the pump inlet so as to return the piston to a rest position when the solenoid coil is deactivated, the pump being equipped with a suitable one-way valve (not shown) and exhaust port (represented at 88 in FIG. 4) for permitting return of the piston to its rest position without requiring the sampled gas to be expelled through the sample port 72 back into the sample chamber 56.

The sample tank 16 also includes an electronic interface module 90 having the plug J4 mounted thereto for receiving the cable socket 53 of the signal cable 44, the interface module 90 having circuits described herein for interfacing the various breath sensor elements described above, and preferably one or more ambient sensors. As shown in FIG. 4, the interface module 90 includes an ambient temperature circuit 93 (further described below in connection with FIG. 9) for interfacing an ambient temperature sensor 94. There is also a heater driver 95 (which can be simply a power FET driver transistor and input biasing resistor) for activating the bearing coil 75, and a pump driver 96 (further described below in connection with FIG. 8) for powering the solenoid coil 87. The sample unit 16 also includes a keypad 97 for receiving operator input, and an LCD display 98 for indicating various responses and operating states of the interlock system. The display 98 is connected by a separate plug (DO, not shown) through the cable 44 to another separate socket (J2, not shown) of the base unit 14. If desired, the display 98 can also be located separately or remotely from the sample unit 16. Further, an optional external interface 99 facilitates calibration and maintenance of the sensor unit 16.

Figure 5:
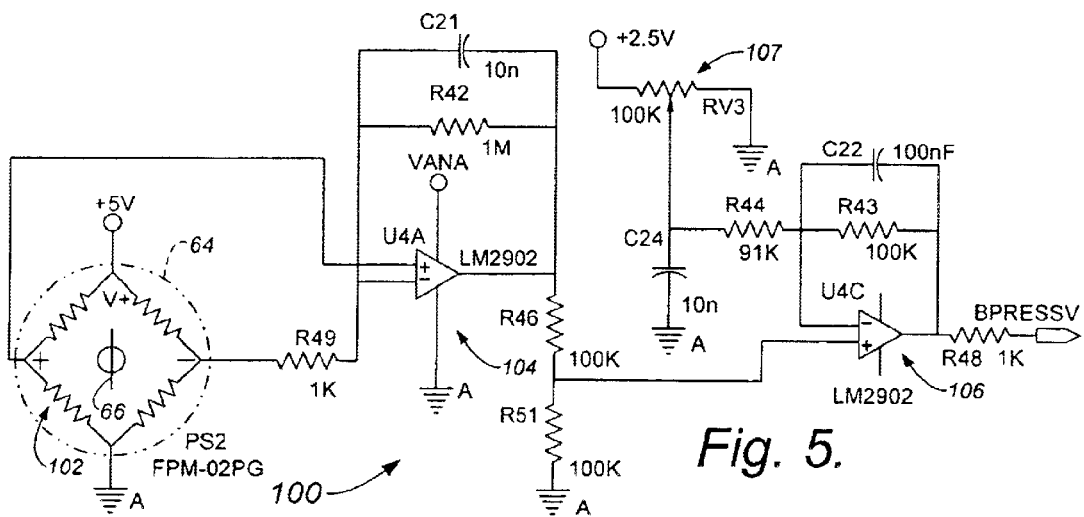
FIG. 5 is a schematic diagram of a breath pressure circuit portion the system of FIG. 4.

More particularly, the breath pressure transducer 64 is connected in a breath pressure circuit 100 as shown in FIG. 5, the transducer 64 including a strain-gauge bridge 102 that feeds a first stage amplifier 104 having a gain of approximately 1000. The first stage amplifier feeds a second stage amplifier 106 of approximately unity gain to produce a BPRESSV output, the amplifier 106 having a baseline adjustment 107. It will be appreciated that the exact gain of the pressure circuit 100 is not critical, in that the primary purpose of the pressure transducer 64 is to detect a threshold dynamic blowing pressure of a breath sample and maintenance of at least that pressure during a sampling interval of the apparatus 10. Thus it is important that the gain be sufficiently high for adequate sensitivity, and that the dynamic range be sufficiently broad to encompass that threshold. Further, for reasons developed below, it is also important that the gain be reasonably linear and that the dynamic range extend above the threshold to encompass any reasonably expected maximum dynamic pressure to be encountered during the sample interval and, preferably, to allow for programmable adjustment of the threshold such as for accommodating users with medical conditions (asthma, for example) that would affect normal breathing. A device suitable for the breath pressure transducer 64 is commercially available as Model FPM-02PG also available from Alcohol Countermeasure Systems Corp. An integrated circuit device suitable for use as active portions of the first and second amplifiers 104 and 106 is available as an LM2902 Quad Operational Amplifier from National Semiconductor of Santa Clara, Calif., and a variety of other sources (half of the device being used in the pressure circuit 100).

Figure 6:
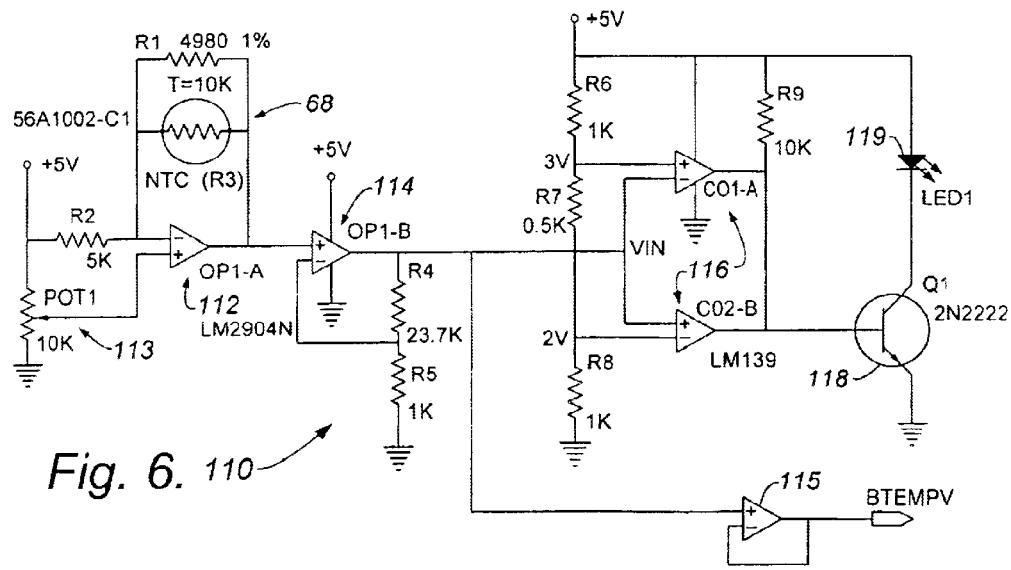
FIG. 6 is a schematic diagram of a breath temperature circuit portion of the system of FIG. 4.

The breath temperature sensor 68 is connected in a breath temperature circuit 110 as shown in FIG. 6, variably shunting the feedback path of a third amplifier 112 having an offset adjustment 113. A device particularly suitable for use as the sensor 68 is a negative temperature coefficient (NTC) chip thermistor, which has a high sensitivity response to temperature, one preferred device of this type being available as Part No. 56A1002-C1 from Alpha Sensors, Inc. of San Diego, Calif. The output of the third amplifier 112 is connected to a voltage amplifier 114 that feeds an analog output buffer 115 (having a BTEMPV output) and a pair of comparators 116 that are connected for activating an output transistor 118 to illuminate a light-emitting diode (LED) 119 when the output of the voltage amplifier 114 (and the BTEMPV output) is between approximately two volts and approximately three volts, those values corresponding to a relatively narrow range of temperatures that are associated with human breath samples. The third amplifier 112 and the voltage amplifier 114 can be implemented using elements of a quad integrated circuit amplifier such as the LM2904 device described above. The comparators 116 can be elements of a quad integrated circuit comparator such as the LM139 device that is also available from a variety of commercial sources. The output of the analog buffer 115 is used in combination with the humidity sensor 70 for enhanced verification (screening) of human breath samples, and for enhanced accuracy in measuring breath alcohol (BAC) levels as described below.

Figure 7:
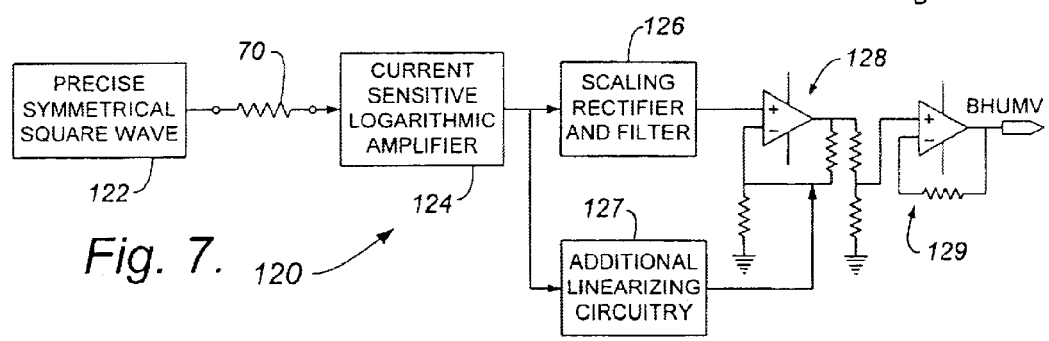
FIG. 7 is a simplified schematic diagram of a breath humidity circuit portion the system of FIG. 2.

The humidity sensor 70 is connected in a breath humidity circuit 120 as shown in FIG. 7. An inexpensive sensor suitable for use as the humidity sensor 70 has been available as Model PCRC-55, from Phys-Chemical Research Corp. (PCRC) of Now York, N.Y.; a similar device, No. HC-800, is available from Ohmic Instruments, Co. of Easton, Md. The humidity sensing portion of this sensor, an outer surface layer of a styrene copolymer, advantageously produces a very quick response time on the order of a few seconds. It does, however, have a positive temperature coefficient of 0.36 RH unit/degree Celsius. Accordingly, the humidity circuit 120 includes a temperature-compensated square-wave oscillator 122 that excites the sensor 70 with a current that is fed into a logarithmic amplifier 124, the amplifier compensating significant non-linear behavior of the sensor 70. The output of the logarithmic amplifier 124 feeds a conditioning amplifier 126 which drives a breakpoint amplifier 127 and an operational amplifier 128. The output of the breakpoint amplifier 127 is fed into the feedback path of the operational amplifier 128 to provide further non-linear compensation of the sensor 70 below 40% relative humidity (RH). The operational amplifier 128 feeds a scaling buffer amplifier 129 to provide a 5-volt full scale BHUMV output, the operational amplifier 128 having a full scale output of ten volts for facilitating calibration of the non-linear compensation for the sensor 70.

The oscillator 122 produces a square wave of fixed frequency and amplitude and having no DC component, being symmetrical about ground potential for prevention of detrimental electrochemical migration. Further details and appropriate calibration and adjustment of the humidity circuit 120 are described in Application Note 256, entitled "Circuitry for Inexpensive Relative Humidity Measurement" (National Semiconductor, 1981).

The alcohol sensor 80 is connected in a breath alcohol circuit 130. As shown in FIG. 3, the sensor is loaded with 330 ohms by R24, and selectively subjected to a virtual short circuit in response to an external signal FCSHRT by a FET transistor Q5. An operational amplifier 132 provides voltage gain, the output of the amplifier 132 feeding an integrating voltage follower 134 having a BACV output that has a time constant of approximately 10mS. The voltage follower 134 produces approximately 0.8V when the BAC is 0.05% and approximately 1.6V when the BAC is 0.1%.

Figure 8:
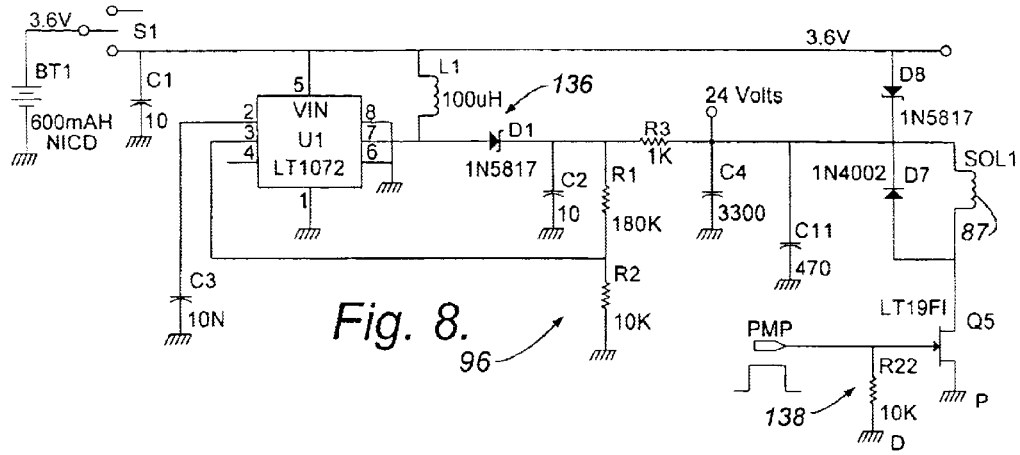
FIG. 8 is a schematic diagram of a breath sample pump circuit portion the system of FIG. 4.

The solenoid coil 87 of the pump 86 is driven by a pump driver circuit 96 as indicated above and shown in FIG. 8, the circuit 96 having a voltage multiplying DC to DC converter 136 for generating approximately 24V from the vehicle battery 26 or, as shown in FIG. 8, a rechargeable battery 137 (which was introduced above and is shown in FIG. 4 as external to both the base unit 14 and the sensor unit 16, it being understood that the location of the rechargeable battery is not critical). The converter 136 feeds a power inverter 138 that selectively applies the 24V to the coil 87 in response to an external PMP signal.

Figure 9:
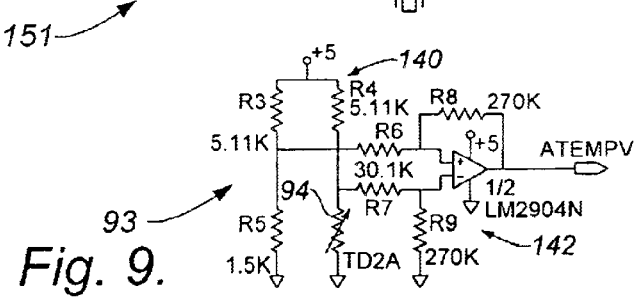
FIG. 9 is a schematic diagram of an ambient temperature circuit of the system of FIG. 4.

The ambient temperature circuit 93, shown in FIG. 9, includes a resistive bridge circuit 140 having the ambient temperature sensor 94 in one leg thereof, respective output nodes of the network 140 being resistively coupled to complementary inputs of a differential operational amplifier 142 having an ATEMPV output. Devices suitable for use as the ambient temperature sensor 94 are available as TD2A (and TD5A) negative coefficient thermistor from Microswitch Corp. of Morristown, N.J. With the gain of the operational amplifier set at 10 (R8/R6+1), and using resistors having 1% tolerance, the output of the amplifier 142 at room temperature (20° C. or 68° F.) is approximately 2.7V, the sensor having a room-temperature resistance of approximately 2K ohms. The sensor 94 advantageously has a slow response time on the order of one minute so as to be insensitive to momentary power fluctuations within the sample unit 16. Also, as further described below, the sensor 94 is located close to both the sample tube 54 (and the sample chamber 56) and the alcohol sensor 80, for measurement of a "locally ambient" temperature which can be significantly higher than the temperature outside the sensor unit 16 at relatively cold temperatures calling for heating of the sample tube 54 as well as occasions of heating by the heating coil 75 for accelerated purging of the alcohol sensor 80. At higher outside ambient temperatures relevant to adjustment of qualifying breath temperatures and moisture contents, the measured locally ambient temperature more closely matches the outside ambient temperature.

In addition, the sample module 16 also has a power switch 146 that can be mechanically or magnetically coupled to a moveable cover or lid 148 that is displaced to uncover the keypad 97 and the LCD display 98 and produce an OPN signal when the interlock system 10 is to be actuated.

Figure 10:
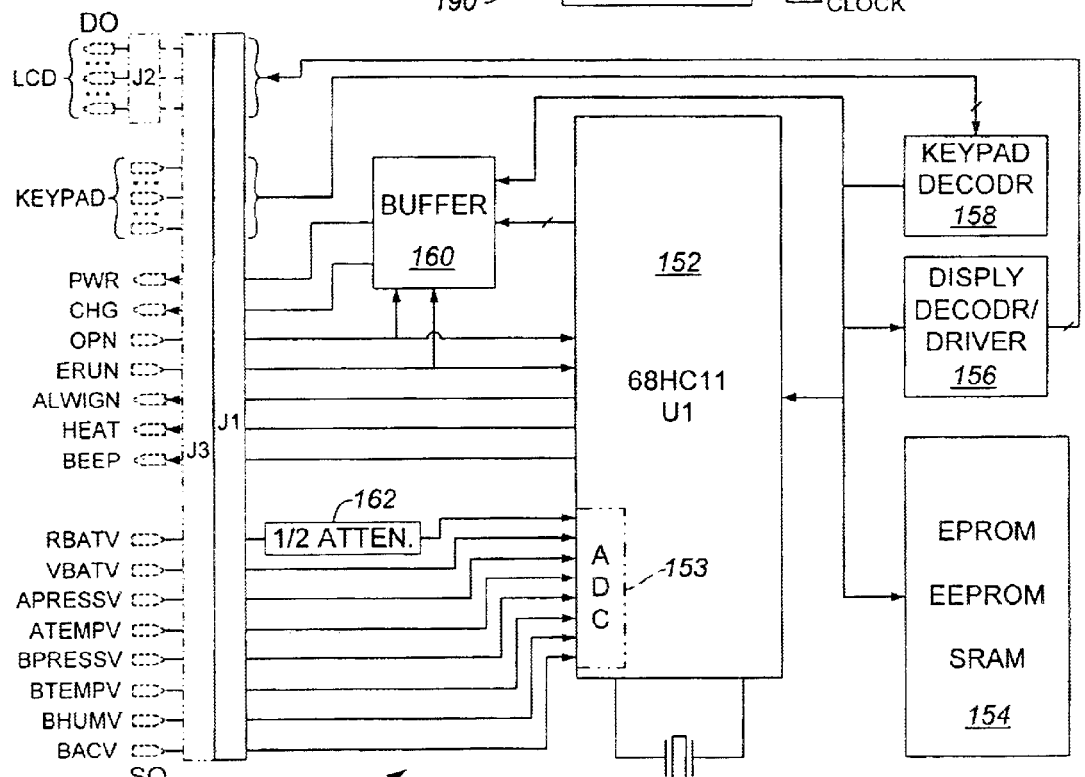
FIG. 10 is a simplified block diagram of a control module of the system of FIG. 4.

The respective outputs of the ambient temperature circuit 93, the breath pressure circuit 100, the breath temperature circuit 110, the breath humidity circuit 120, and the breath alcohol circuit 130, as well as inputs of the heater driver 95 and the pump driver circuit, are connected through the signal cable 44 to a control module 150 that is located in the base unit 14, as further described herein in connection with FIG. 10. The control module 150 is situated in the base unit 14 together with the power board module 51 and is connected thereto by a ribbon cable (not shown) between a connector J1 of the control module 150 and a connector J3 of the power module 51. The connector SO to which the signal cable 44 is connected is located on the power module 51, with connections to the control board 150 being completed via J1 and J3. Similarly, the connector J2 for signals to the LCD display 98 is located on the power module, the connections thereto being made through the connectors J1 and J3 and the interconnecting ribbon cable. It will be understood that the display decoder/driver 156 can be located on the power module 51 in order to conserve conductors of the connectors J1 and J3, as well as of the ribbon cable. A control circuit 151 of the control board includes a microprocessor 152 having associated memory 154 (which can include EPROM, EEPROM, and SRAM), a display decoder/driver 156, a keyboard interface 158, and a buffer 160 (which can include several "type D" flip-flops, as they are commonly known, and associated logic.

The microprocessor 152 is preferably of the type having on-board analog to digital (ADC) conversion of multiple signals as indicated at 153 in FIG. 10, such a device being commercially available as Model 68HC11 control processor, from Motorola Corp. of Phoenix, AZ. As shown in FIG. 10, each of the analog outputs ATEMPV, BPRESSV, BTEMPV, BHUMV, and BACV from the above described circuits of the sample unit 16 are fed into the ADC 153 of the microprocessor 152. in addition, the ADC receives an optional altitude pressure signal APRESSV from the power module 51, as well as attenuated battery voltages VBATV and RBATV of the vehicle battery 26 and the rechargeable battery 137, also from the power module 51. As shown in FIG. 10, an attenuator 162 is interposed between the RBATV signal and the ADC 153 to scale the ADC input to within its 5V range; the attenuator can include a voltage divider that preferably feeds a voltage follower in a conventional manner. The OPN signal from the power switch 146, and an engine run signal ERUN (described below) from the power module 51 are connected both to the microprocessor 152 and the buffer 160, the buffer also being connected to the microprocessor and having a PWR output that is activated upon opening of the lid 148 to expose the keypad 97 and the LCD display 98, the PWR output remaining active until terminated by the microproccessor 52. The buffer 160 is also responsive to the microprocessor 152 for producing a CHG signal to activate charging of the rechargeable battery as described below. Other outputs of the microprocessor 152 include an ALWIGN, signal for enabling activation of the first relay 46 (see FIG. 4), a HEAT signal for activating the heating coil 75 in the sample unit 16 as further described below, and a BEEP signal for activating a suitable beeper 163 (which can be located externally of the base unit 14 as shown in FIG. 4). The beeper 163, which can include a piezoelectric transducer, is activated with a series pulses for prompting operator response, such as at periodic intervals during operation of the vehicle when it may be requited to conduct a "rolling" breath test to verify that the driver of the vehicle 12 has not become intoxicated subsequent to starting the vehicle.

Figure 11:
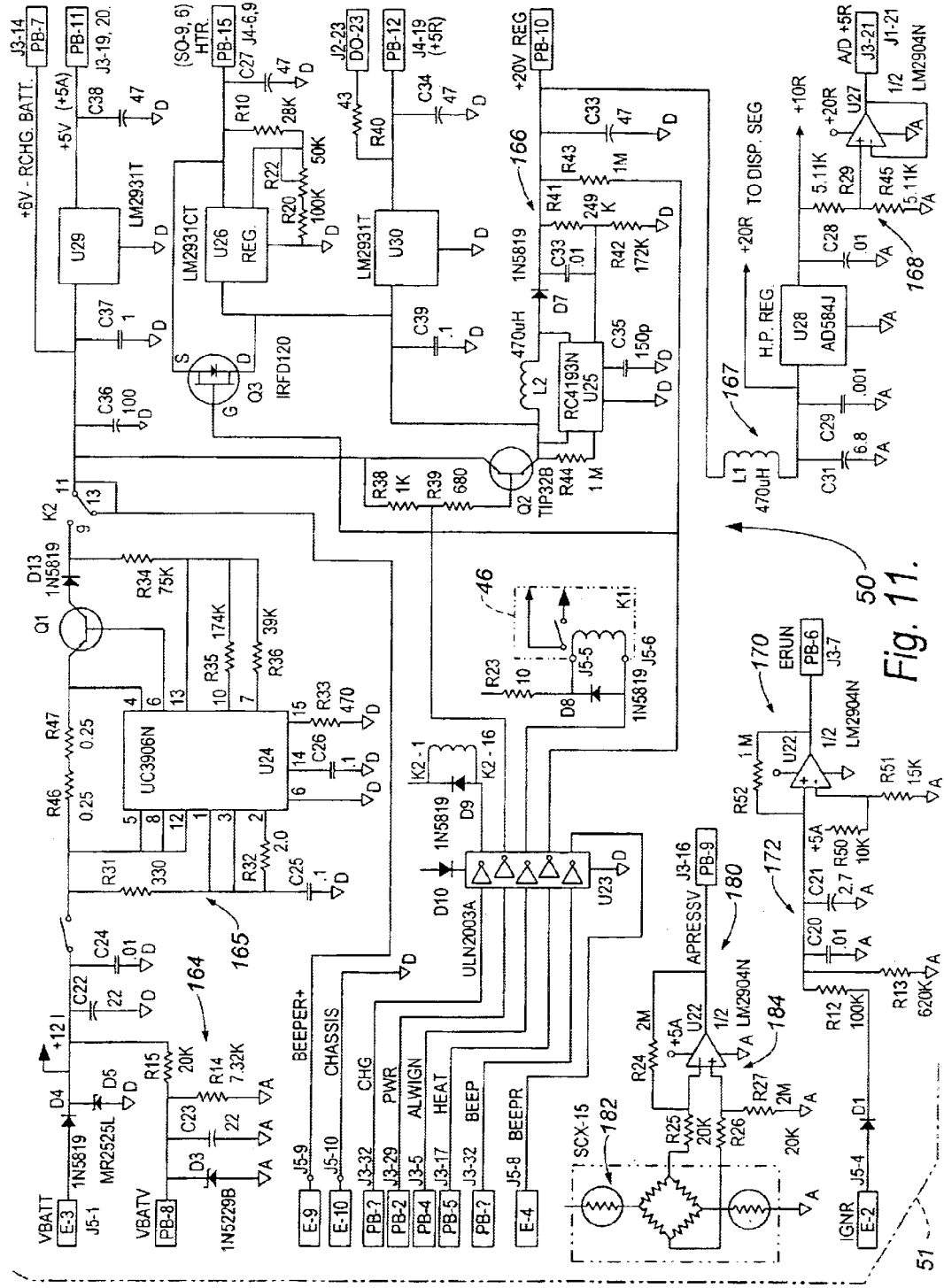
FIG. 11 is a schematic diagram of a power section circuit of the system of FIG. 4.

As shown in FIG. 11, the power circuit 50 includes a vehicle battery attenuator 164 connected to the vehicle battery 26 (VBATT) for producing the VBATV signal within the 5V range of the ADC 153. The vehicle battery (VBATT) feeds a charger circuit 165 having a conventional configuration, the exemplary form thereof shown in FIG. 11 having a Unitrode (Texas Instrument) UC3906N battery charger device which is representative of such circuits that are commercially available from a variety of sources. The charger circuit 165 is connected to the rechargeable battery 137 through contacts of the second relay 47, the battery 137 powering a first regulator U29 that always provides 5V (+5A), a second regulator U26 that provides the HTR signal to the heating coil 75 in response to the PWR and HEAT signals from the control module 150, and a third regulator U30 that is activated by the PWR signal. A fourth regulator U28 that is powered at 20V by a converter circuit 166 and filter 167 provides 10V for use as described below, the fourth regulator U28 also feeding a voltage follower U27 through a divider 168 to provide a 5V reference (A/D+5R) to the ADC 153. An inverting buffer U23 isolates the CHG, PWR, and HEAT signals from the control module 150, as well as activating the first relay 46 in response to the ALWIGN signal, and activating a BEEPR output to the beeper 163 in response to the BEEP signal, the ALWIGN and BEEP signals also being from the control module 150.

The power module 51 also includes an engine run circuit 170 that is responsive to the voltage (IGNR) at the run terminal 42 of the ignition switch (see FIG. 4). The engine run circuit 170 has a voltage dividing filter 172 that feeds a comparator amplifier U22 having an ERUN output. The ERUN output is activated for as long as the voltage IGNR is sufficient, allowing for negative spikes such as are blocked by the filter 172, to indicate that the ignition switch 38 remains in an on condition.

Optionally, the power module 51 additionally includes a pressure altitude circuit 180 having an ambient pressure transducer 182, the outputs of which feed a differential amplifier 184 for producing the ambient pressure signal APRESSV for receipt by the ADC 153. The APRESSV signal, when implemented, is used by software of the microprocessor 152 to compensate the BACV signal from the breath alcohol circuit 130.

Figure 12:
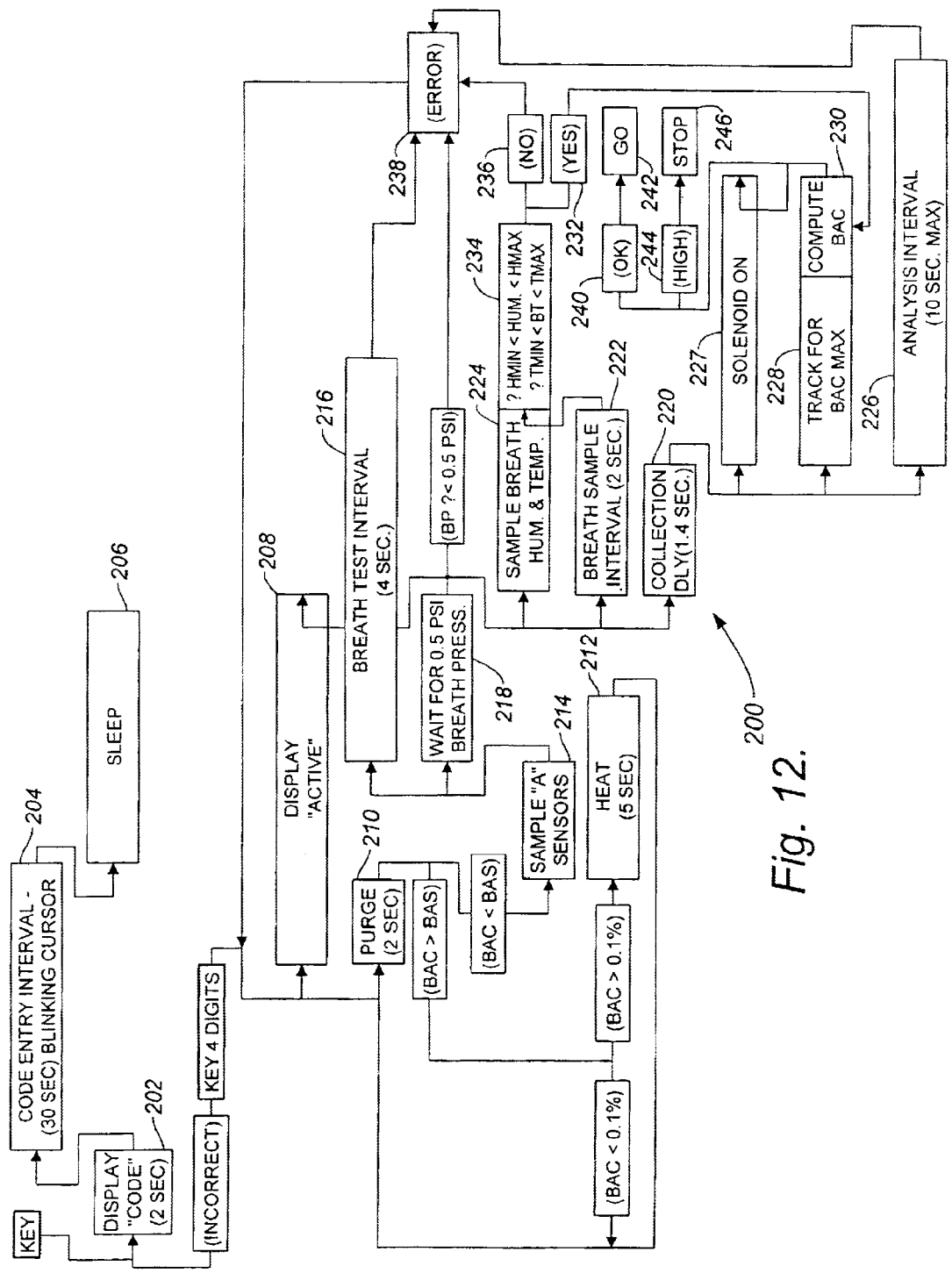
FIG. 12 is a timing diagram of a breath alcohol measuring cycle of the system of FIG. 4.

Operation of the interlock system 10 in a breath alcohol measurement cycle is best understood with particular reference to FIG. 12, which is partly a timing diagram and partly a flow chart. With the lid 148 opened so as to activate the PWR signal as described above, an interlock cycle 200 is initiated by depression of a key of the keypad 97, the LCD display 98 being written in response as indicated at 202 under control of the microprocessor 152 for prompting the user to enter a code of four digits during a code entry interval 204 such as thirty seconds in which a cursor of the display is blinking. Failing correct entry of the code in that interval, the system returns to a "sleep" mode 206 in which the PWR signal is inactive. Upon correct code entry the microprocessor causes an "active" prompt to be displayed as indicated at 208, and the alcohol sensor 80 is purged of alcohol for an interval such as two seconds as indicated at 210 by activation of the FCSHRT input of the breach alcohol circuit 130. If the BAC remains above 0.1% a heating interval 212 is initiated for approximately five seconds and the purge cycle 210 is repeated; if the BAC is less than 0.1% but above a predetermined baseline value, the only purge cycle 210 is repeated, until the BAC is lens than the baseline value, signifying that the alcohol sensor 80 is sufficiently purged, in which case ambient measurements are taken of temperature, humidity and, optionally, pressure, as indicated at 214. Once the ambient measurements are taken, a breath test interval 216 is initiated in which the user is prompted to produce a breath sample by blowing into the mouthpiece 18, and a wait interval 218 is simultaneously activated for the user to produce a threshold breath pressure (nominally 0.5 PSI), whereupon the active prompt 208 is terminated and a collection delay 220 of approximately 1.4 second and a sample interval 222 of approximately two seconds (during which a breath sample is obtained as indicated at 224) are simultaneously initiated. Preferably the sample temperature response time is not greater than approximately one second for providing accurate readings in these advantageously short cycle intervals. An analysis interval 226 having a maximum duration of approximately ten seconds is initiated at the conclusion of the collection delay 220, in which the pump solenoid coil 87 is activated as indicated at 227 and the BACV signal from the breath alcohol circuit 130 is tracked for peak detection as indicated at 228, at which point the BAC is computed as indicated at 230, provided that, following completion of the sample interval 222, the sample is verified as being human as indicated at 232, the breath temperature and humidity both being within a predetermined profile that has been dynamically adjusted to compensate for variations in one or more of the ambient measurements obtained in the ambient measurement interval 214, as indicated at 234.

For example, when the ambient temperature is not within a first temperature range such as between approximately 29.5° C. and approximately 39.5° C., the valid sample temperature range can be relaxed (expanded), such as from between approximately 32.5° C. and approximately 36.5° C. to between approximately 30.5° C. and approximately 38.5° C. In another example, when the ambient temperature is not above a predetermined threshold such as 80° F. (26.6° C.), the valid sample temperature range can be relaxed (expanded). Also, when the ambient humidity is equal or greater than the sample humidity the valid sample moisture content range can be relaxed (expanded) such as from between approximately 67% and 73% RH to between approximately 65% and 75% RH. In a further example, the valid range of the determined sample temperature can be dependent on the ambient temperature and the valid range of the sample moisture content can be dependent on the ambient humidity. In yet another example, the valid range of the determined sample temperature can be dependent on the ambient humidity and the valid range of the sample moisture content can be dependent on the ambient temperature. The solenoid coil 87 is deactivated upon completion of the BAC computation (and the alcohol sensor 80 as purged as previously indicated at 210) for prompt readiness for a subsequent measurement cycle, if required.

If the breath pressure fails to reach 0.5 psi. if the sample is determined to be non-human as indicated at 236, if the breath test interval 216 times out before the sample interval 222, or if the analysis interval 226 times out before completion of the BAC computation, an error condition 238 is reached, at which point the cycle must be repeated before operation of the vehicle 12 is enabled. Otherwise, if the measured (and compensated) BAC is within a predetermined limit, such as 0.08%, as indicated at 240, operation of the vehicle 12 is enabled as indicated at 242, by activating the first relay 46 as described above. However, if the BAC exceeds the predetermined limit as indicated at 244, operation (starting) of the vehicle is not enabled as indicated at 246 and, preferably, the user is prompted (not shown) that the vehicle will be disabled once it is stopped. The microprocessor 152 is preferably also programmed for requiring initiating "rolling tests" at predetermined intervals during operation of the vehicle 12, using means that are within the ordinary skill of those in the art.

Figure 13:
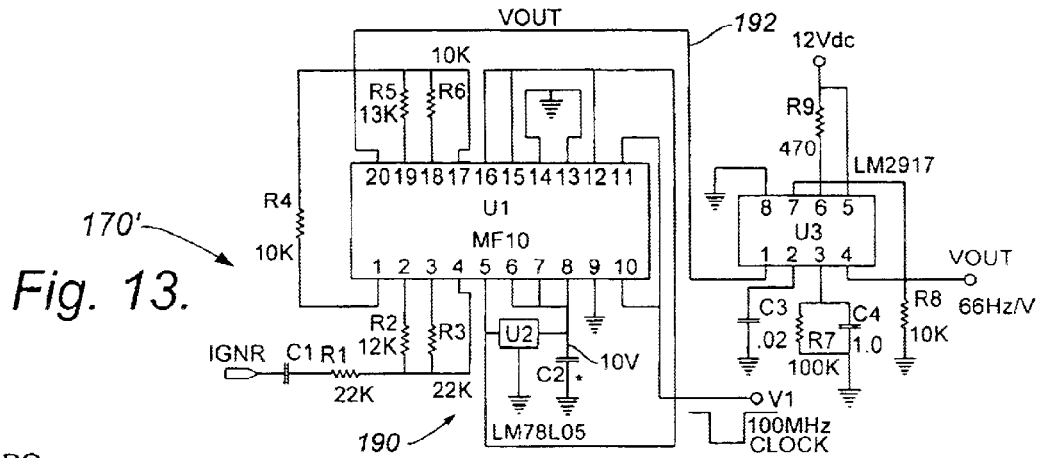
FIG. 13 is a schematic diagram showing an alternative configuration of an engine run circuit portion of the power section circuit of FIG. 9.

With further reference to FIG. 13, a preferred alternative configuration of the engine run circuit, designated 170', includes an active filter circuit 190 that incorporates a monolithic active filter building block MF10, which is available from National Semiconductor and is more fully described in Application Note 307, dated 1995 and available from the same source. The active filter circuit 190 receives the IGNR signal from the ignition switch 38 as described above, and is clocked at 100 MHz as shown in FIG. 13 in any suitable manner, to produce a low-pass output 192. The circuit 190, requiring only a single supply voltage, provides a 1KHz fourth-order Butterworth filter that detects the presence of alternator noise at the ignition switch 38, the alternator noise having a rectified AC profile of approximately 0.3V amplitude at frequencies ranging upwardly from approximately 400Hz. The supply voltage of 10V, indicated as being supplied by U2 in FIG. 13, can be provided by the fourth regulator U28 of FIG. 11. The low pass output 192 feeds a frequency to voltage converter U3, such as an LM 2917N which is available from National Semiconductor, the converter U3 being preferably configured for saturation at a relatively low speed of the vehicle engine 22, thereby to deliver the ERUN output as essentially a digital signal that is indicative of the engine running, as opposed to being merely indicative of the ignition switch 38 being on as in the engine run circuit 170 of FIG. 11.

Although the present invention has been described in considerable detail with reference to certain preferred versions thereof, other versions are possible. For example, the power interlock circuit can be connected in any suitable way to a vital subsystem of the vehicle 12 or other equipment being protected by the system 10, in order to inhibit operation of the equipment. Therefore, the spirit and scope of the appended claims should not necessarily be limited to the description of the preferred versions contained herein.

What is claimed is:

1. A breath measurement instrument comprising:
   (a) means for receiving a breath sample; and
   (b) means for validating the sample, comprising:
      (i) means for detecting the breath sample based on maintenance of a predetermined minimum dynamic pressure over a predetermined minimum sample interval;
      (ii) means for determining a sample temperature of the sample;
      (iii) means for determining a sample moisture content of the sample;
      (iv) means for measuring at least one of an ambient temperature and an ambient humidity; and
      (v) means for comparing the determined sample temperature and moisture content with a predetermined profile of valid temperatures and moisture contents, validation being blocked unless the determined temperature and moisture content is within the predetermined profile, wherein the predetermined profile includes a valid temperature range of the determined sample temperature and a valid humidity range of the determined sample humidity, at least one of the valid ranges being dependent on at least one of the ambient temperature and the ambient humidity.

2. The instrument of claim 1, wherein the means for receiving the breath sample comprises a tubular conduit having a mouthpiece extremity, the conduit defining a sample passage.

3. The instrument of claim 2, wherein the means for determining the sample temperature comprises a sample temperature sensor supported relative to the tubular conduit and projecting into the sample passage, and a sample temperature circuit having a sample temperature output, the sample temperature sensor and the sample temperature circuit together having a sample temperature response time.

4. The instrument of claim 3, wherein the valid range of the determined sample temperature is a first temperature range when the ambient temperature is within a predetermined ambient temperature range, the valid temperature range being otherwise a second temperature range, the first temperature range being within the second temperature range.

5. The instrument of claim 4, wherein the first temperature range is from approximately 32.5° C. to approximately 36.5° C., the second temperature range is from approximately 30.5° C. to approximately 38.5° C., and the ambient temperature range is from approximately 29.5° C. to approximately 39.5° C.

6. The instrument of claim 3, wherein the valid range of the determined sample temperature is a first temperature range when the ambient temperature is not greater than a predetermined threshold ambient temperature, the valid temperature range being otherwise a second temperature range, the first temperature range being within the second temperature range.

7. The instrument of claim 6, wherein the threshold ambient temperature is approximately 80° F. (26.6° C.).

8. The instrument of claim 3, further comprising means for signifying at least an out-of-limit temperature and an in-limit temperature of the breath sample.

9. The instrument of claim 3, wherein the sample temperature response time is not greater than approximately one second.

10. The instrument of claim 3, wherein the means for measuring ambient temperature comprises an ambient temperature sensor located externally of the sample passage and an ambient temperature circuit having an ambient temperature output, the ambient temperature sensor and the ambient temperature circuit together having an ambient temperature response time being greater than the sample temperature response time.

11. The instrument of claim 10, wherein the sample temperature response time is not greater than approximately one second and the ambient temperature response time is nor less the approximately one minute.

12. The instrument of claim 2, wherein the means for determining humidity comprises a humidity sensor supported relative to the tubular conduit and projecting into the sample passage, and a humidity circuit having a sample humidity output.

13. The instrument of claim 12, wherein the valid range of the determined sample moisture content is a first moisture range when the ambient humidity is less than the sample moisture content, the valid moisture content range otherwise being a second moisture range, the first moisture range being within the second moisture range.

14. The instrument of claim 13, wherein the first moisture range is from approximately 67% RH to approximately 73% RH, and the second moisture range is from approximately 65% RH to approximately 75% RH.

15. The instrument of claim 12, further comprising means for signifying at least an out-of-limit humidity and an in-limit humidity of the breath sample.

16. The instrument of claim 12, wherein the means for measuring the ambient humidity comprises means for sampling the sample humidity output as an ambient humidity output prior to receiving a breath sample.

17. The instrument of claim 1, wherein the valid range of the determined sample temperature is dependent on the ambient temperature and the valid range of the sample moisture content is dependent on the ambient humidity.

18. A breath alcohol instrument comprising the breath measurement instrument of claim 1 in combination with means for determining an alcohol content of the sample.

19. The breath alcohol instrument of claim 18, wherein the means for determining the alcohol content comprises an alcohol-specific fuel cell.

20. The breath alcohol instrument of claim 19, further comprising a fuel cell circuit for producing a breath alcohol signal, and means for compensating the breath alcohol signal in response to variations in one or more variables of the set consisting of ambient temperature, ambient pressure, sample temperature, and sample humidity.

21. The breath alcohol instrument of claim 20, wherein the means for receiving the breath sample comprises a tubular conduit having a mouthpiece extremity, the conduit defining a sample passage, wherein the means for measuring ambient temperature comprises an ambient temperature sensor located proximate the fuel cell and the tubular conduit for sensing a locally ambient temperature, the instrument further comprising a heater element in thermal communication with the tubular conduit, and wherein the means for compensating the breath alcohol signal comprises means for controllably powering the heater element in response to the ambient temperature sensor.

22. A breath alcohol interlock device for preventing use of a machine by an intoxicated operator, comprising the breath alcohol instrument of claim 18 in combination with an interlock circuit for disabling the machine except upon validation of a breath sample having an alcohol content below a predetermined amount.

23. The instrument of claim 1, wherein the valid range of the determined sample temperature is dependent on the ambient humidity and the valid range of the sample moisture content can be dependent on the ambient temperature.

24. A breath alcohol interlock device for preventing use of a machine by an intoxicated operator, comprising:

(a) means for receiving a breath sample, comprising a tubular conduit having a mouthpiece extremity, the conduit defining a sample passage;

(b) means for validating the sample, comprising:

(i) a pressure transducer including an actuator projecting into the sample passage and apparatus converting for generating a sample pressure signal in response to dynamic gas pressure against the actuator for detecting the breath sample based on maintenance of a predetermined minimum dynamic pressure over a predetermined minimum sample interval;

(ii) means for determining a sample temperature of the sample, comprising a sample temperature sensor supported relative to the tubular conduit and projecting into the sample passage, and a sample temperature circuit having a sample temperature output;

(iii) means for determining a sample moisture content of the sample, comprising a humidity sensor supported relative to the tubular conduit and projecting into the sample passage, and a humidity circuit having a sample humidity output, the humidity sensor and humidity circuit output being operative for providing an ambient humidity measurement prior to receipt of the breath sample;

(iv) an ambient temperature sensor located proximate the tubular conduit and an ambient temperature circuit responsive thereto and having an ambient temperature output;

(v) a heater element in thermal communication with the tubular conduit; and (vi) a processor for comparing the determined sample temperature and moisture content with a predetermined profile of valid temperatures and moisture contents in response to the sample temperature and humidity outputs and the ambient temperature output, validation being blocked unless the sample temperature and the sample moisture content are within the predetermined profile, wherein the predetermined profile includes a valid range of the determined sample temperature that is dependent on the ambient temperature and a valid humidity range of the sample moisture content that is dependent on the ambient humidity;

(c) an alcohol-specific fuel cell and a fuel cell circuit for producing a breath alcohol signal, the processor being operative for activating the heater element in response to the ambient temperature sensor to selectively maintain a predetermined minimum ambient temperature proximate the sample passage for compensating the breath alcohol signal in response to ambient temperature, the processor also determining an alcohol content of the sample; and (d) an interlock circuit for disabling the machine in response to the processor except upon validation of a breath sample having an alcohol content below a predetermined amount.

25. A method for screening breath samples and determining an alcohol content thereof, comprising:
   (a) receiving a breath sample;
   (b) validating the sample, comprising:
      (i) determining a sample temperature of the sample;
      (ii) determining a moisture content of the sample;
      (iii) measuring at least one of an ambient temperature and an ambient humidity;
      (iv) comparing the determined sample temperature and moisture content with a predetermined profile of valid temperatures and moisture contents; and
      (v) blocking the validation unless the determined temperature and moisture content is within the predetermined profile, wherein the predetermined profile includes a valid temperature range of the sample temperature that is dependent on the ambient temperature, and a valid determined sample moisture content that is dependent on ambient humidity;
   (c) determining an alcohol content of the sample, comprising producing a breath alcohol signal responsive to the alcohol content of the sample; and
   (d) compensating the breath alcohol signal in response to variations in one or more variables of the set consisting of ambient temperature, ambient pressure, sample temperature, and sample humidity.

26. The method of claim 25, wherein the determining the alcohol content comprises using an alcohol-specific fuel cell.

* * * * *

UNITED STATES PATENT AND TRADEMARK OFFICE
CERTIFICATE OF CORRECTION

| | |
|---|---|
| PATENT NO. | : 6,792,793 B2 |
| DATED | : September 21, 2004 |
| INVENTOR(S) | : Mendoza, Joaquin L. |

It is certified that error appears in the above-identified patent and that said Letters Patent is hereby corrected as shown below:

<u>Title page,</u>
Item [73], Assignee, change "Ignition Lock International" to -- Ignition Interlock International --

<u>Drawings,</u>
FIG. 4, The REG block should be item 28.

<u>Column 3,</u>
Line 11, replace "additional a test reading" with -- additional test reading --

<u>Column 4,</u>
Line 46, replace "breath alcohol levels due variations" with -- breath alcohol levels due to variations --

<u>Column 6,</u>
Line 16, replace "portion the system of" with -- portion of the system of --
Line 20, replace "humidity circuit portion the system" with -- humidity circuit portion of the system --
Line 22, replace "circuit portion the system" with -- circuit portion of the sysstem --
Line 35, replace "section circuit of FIG. 9" with -- section circuit of FIG. 11 --

<u>Column 7,</u>
Line 7, replace "has a housing 43 and circuit" with -- has a housing 45 and circuit --
Line 8, replace "in the form of first second, and" with -- in the form of first, second, and --
Line 31, replace "adapted for sealingly extending" with -- adapted for sealing and extending --

<u>Column 8,</u>
Line 20, replace "bearing coil" with -- heating coil --

<u>Column 11,</u>
Line 38, replace "may be requited to" with -- may be required to --

<u>Column 12,</u>
Line 20, replace "input of the breath alcohol circuit" with -- input of the breath alcohol circuit --
Line 38, replace "until the BAC is lens than the" with -- until the BAC is less than the --
Line 48, replace "approximately 1.4 second and" with -- approximately 1.4 seconds and --

UNITED STATES PATENT AND TRADEMARK OFFICE
CERTIFICATE OF CORRECTION

PATENT NO. : 6,792,793 B2
DATED : September 21, 2004
INVENTOR(S) : Mendoza, Joaquin L.

It is certified that error appears in the above-identified patent and that said Letters Patent is hereby corrected as shown below:

Column 13,
Line 48, replace "sensor 80 purged as" with -- sensor 80 has purged as --

Column 16,
Line 44, replace "a beater element in thermal" with -- a heater element in thermal --

Column 18,
Line 13, replace "wherein the determining the alcohol" with -- wherein the determining of the alcohol --

Signed and Sealed this

Twenty-eighth Day of June, 2005

JON W. DUDAS
*Director of the United States Patent and Trademark Office*